(12) United States Patent
Zhang et al.

(10) Patent No.: US 7,094,228 B2
(45) Date of Patent: Aug. 22, 2006

(54) METHODS AND FORMULATIONS FOR PHOTODYNAMIC THERAPY

(75) Inventors: Jie Zhang, Salt Lake City, UT (US); Larry Rigby, Salt Lake City, UT (US); Wade Hull, Taylorsville, UT (US)

(73) Assignee: Zars, Inc., Salt Lake City, UT (US)

( * ) Notice: Subject to any disclaimer, the term of this patent is extended or adjusted under 35 U.S.C. 154(b) by 400 days.

(21) Appl. No.: 10/208,662

(22) Filed: Jul. 30, 2002

(65) Prior Publication Data

US 2003/0093057 A1  May 15, 2003

Related U.S. Application Data

(60) Provisional application No. 60/309,040, filed on Jul. 31, 2001.

(51) Int. Cl.
*A61M 31/00*  (2006.01)

(52) U.S. Cl. .......................................... 604/500

(58) Field of Classification Search ............. 604/20–22, 604/19, 890, 1, 289, 291, 304
See application file for complete search history.

(56) References Cited

U.S. PATENT DOCUMENTS

| 5,445,608 | A | * | 8/1995 | Chen et al. | .................... 604/20 |
| 5,814,008 | A | * | 9/1998 | Chen et al. | .................... 604/21 |
| 6,334,856 | B1 | * | 1/2002 | Allen et al. | .................. 604/191 |
| 6,582,724 | B1 | * | 6/2003 | Hsu et al. | .................... 424/449 |

* cited by examiner

*Primary Examiner*—Manuel Mendez
(74) *Attorney, Agent, or Firm*—Thorpe North & Western, LLP

(57) ABSTRACT

An apparatus to rapidly deliver a drug to a patient, the invention comprising the method of locating a drug beneath a patient's skin in a drug depot site, placing a heating component near the drug depot site and generating heat in and near the drug depot site. A control component connected to the heating component is used to control the magnitude and duration of heat generated by the heating component.

25 Claims, No Drawings

METHODS AND FORMULATIONS FOR PHOTODYNAMIC THERAPY

RELATED APPLICATION

This application claims priority to provisional application Ser. No. 60/309,040, filed Jul. 31, 2001, entitled "Methods and Formulations for Photodynamic Therapy."

BACKGROUND

1. Field of the Invention

The present invention is directed toward an apparatus and formulation for photodynamic therapy. More specifically, the invention is directed toward photodynamic therapies that include the use of controlled heat, local anesthetic-photosensitizer combined formulation, pH manipulation, and/or the solidification of the formulation after application.

2. Background

Photodynamic therapy uses photosensitizers activated by light to induce cell death via the formation of single oxygen or other free radicals. Photodynamic therapy is increasingly used to treat skin cancer, psoriasis, and other skin disorders. In a typical treatment, a formulation containing a photosensitizer is applied on the skin or other tissue to deliver the photosensitizer into the tissues by permeation. Light of proper wavelengths is then applied onto the treated tissue. The photosensitizers in the tissue cells are broken by the light to release single oxygen or other free radicals which kill the tissue cells. One commonly used photosensitizer is delta-aminolevulinic acid (ALA). It is desirable to deliver a local anesthetic agent to a patient's skin when the patient is undergoing a procedure using a photosensitizer. This can reduce or eliminate the pain caused by the single oxygen or other free radicals produced by the light treatment. In some cases, the anesthetic is administered after the delivery of the photosensitizer and before the light treatment requiring an additional procedure and/or additional waiting time.

There are several problems associated with the current photodynamic therapy methods and formulations involving ALA or its derivatives (such as methyl, ethyl or propyl esters): 1) It takes at least 4–6 hours of contact time to deliver sufficient amount of ALA into the tissues 2) the penetration of ALA into the treated tissues sometimes is not deep enough, 3) single oxygen or free radicals released by the light in the tissues causes pain, and 4) in some of the currently used formulations (2) of ALA are chemically unstable.

SUMMARY AND OBJECTS OF THE INVENTION

It is thus more desirable to deliver a local anesthetic agent concurrently with the photosensitizer.

An aspect of this invention is to incorporate a local anesthetic agent into a photosensitizer formulation for reducing or eliminating the pain produced by the photodynamic therapy treatment.

Another aspect of some embodiments of the invention is to provide a low pH formulation comprising water, ALA and a local anesthetic agent such as tetracaine or lidocaine, and to provide a convenient method to increase the pH of the formulation prior to or during the application of the formulation on the tissues to be treated in the photodynamic therapy.

Another aspect of some embodiments of the invention is related to using controlled heat to improve the skin penetration of ALA, its derivatives, or other photosensitizers. The purpose of applying controlled heat is to increase penetration depth of the photosensitizer and to shorten the delivery time necessary to obtain desired penetration depth and/or concentration of the photosensitizer in the tissue.

Another aspect of some embodiments of the invention relates to providing a formulation with a low pH so that ALA or its derivative is chemically stable in the formulation, and increasing the pH of the formulation via a convenient method prior to or during the application to promote the penetration of the photosensitizer into the tissues to be treated.

Yet another aspect of some embodiments of the invention relates to incorporating a local anesthetic agent in the formulation containing the photosensitizer, so that the local anesthetic is delivered into the tissues along with the photosensitizer. This can eliminate or reduce the pain caused by the single oxygen or other free radicals in the photodynamic therapy.

Another aspect of some of the embodiments of the invention relates to providing a formulation comprising ALA or its derivatives and a local anesthetic agent. The pH of the formulation is initially low so that the local anesthetic agent is chemically stable, and is increased via a convenient method prior to the application to a predetermined new pH range that promotes the penetration of the local anesthetic agent and, potentially, the photosensitizer, (depending on the type of photosensitizer) into the tissues to be treated.

An additional aspect of some embodiments of the invention relates to providing a formulation comprising a photosensitizer, a conversion agent (such as a crosslinkable but substantially uncrosslinked polymer), and optionally a local anesthetic agent. The formulation is capable of being converted to a solidified sheet via a convenient method (such as via contact with a crosslinking agent) shortly prior to or during the application to facilitate the removal of the formulation from the tissues.

It is understood that the aforementioned individual aspects (use of controlled heat, local anesthetic-photosensitizer combined formulation, pH manipulation, and the solidification of the formulation) may be combined in various ways to achieve the most desired effects and/or flexibility in the treatment.

DETAILED DESCRIPTION OF THE PREFERRED EMBODIMENTS

ALA is chemically quite stable in aqueous media when the pH of the media is lower than about 3.5 (referred as low pH hereafter) and becomes quite unstable when the pH is increased, especially above 7. The ALA molecule has both an acidic group and a basic group (a zwitterion), meaning there is a pH at which the molecule carries no net charge (isoelectric point). The isoelectric point of ALA is estimated to be around pH 6–6.5. It is believed that a zwitterion molecule has the strongest skin penetrability when the media it is in has a pH at or around its isoelectric point. But unfortunately the isoelectric point of ALA does not occur at a pH that provides good chemical stability. Low pH ALA formulations have been used to for achieving acceptable shelf life.

One embodiment of this invention is to provide an ALA or ALA derivative formulation with low pH, which is more stable than a higher pH formulation during storage, and to provide a method for conveniently increasing the pH of the formulation to near the isoelectric point (referred as high pH hereafter) shortly before or during the application. The increase of the pH may be accomplished by many means, including but not limited to 1) covering the formulation already applied on the tissue with a material impregnated with a base or a buffer with proper pH (i.e. pH 6.5 phosphate buffer), or 2) spraying a base or buffer solution onto the skin tissues before applying the ALA formulation, or 3) spraying a base or buffer solution onto the ALA formulation already applied on the skin.

It is desirable to include a local anesthetic agent in a formulation containing a photosensitizer, so that the local anesthetic agent is delivered into the tissues to be treated concurrently with the photosensitizer. This can reduce or eliminate the pain caused by the single oxygen or other free radicals produced by the light treatment. Although the local anesthetic may be administered after the delivery of the photosensitizer and before the light treatment, it would either require an additional procedure (i.e. injection) and/or additional waiting time (i.e. using a noninvasive local anesthetic delivery system). It is thus more desirable to deliver a local anesthetic agent concurrently with the photosensitizer. However, the local anesthetic agent should be so chosen and the formulation should be so designed that the desired local anesthetic effect is achieved within the time period necessary to deliver sufficient amounts of ALA into the tissues. If the local anesthetic effect is already achieved when or before sufficient amounts of ALA are delivered, the light treatment may commence without waiting for the local anesthetic effect, which is desirable.

Therefore, another embodiment of this invention is to incorporate a local anesthetic agent into a photosensitizer formulation for reducing or eliminating the pain produced by the photodynamic therapy treatment.

Tetracaine is a local anesthetic agent which, when incorporated in a medium comprising water, has good skin penetrability when the medium's pH is higher than about 6.5 but rather poor skin penetrability when the pH is low (i.e. 4.5 or below). However, tetracaine is chemically much more stable at low pH than high pH (i.e. about 7). Therefore, it is desirable to store the formulation containing a photosensitizer and tetracaine in a low pH medium and increase the pH to about 7 shortly before or during the application. Other ester type local anesthetic agents, which have similar chemical instability problem, may also be used in this design. This low-storage-pH/high-application-pH approach may be desirable even if there is no need to improve chemical stability or performance of a particular photosensitizer in the formulation, because it improves stability and performance of tetracaine and other ester type local anesthetic agents. However, double benefits can be obtained when a particular photosensitizer, such as ALA, can also derive better chemical stability and/or skin permeability from this approach. In the case of an ALA-tetracaine combination, a storage pH of about 3 and an application pH of about 6.5–7 would be beneficial for both compounds. Other ester type local anesthetics may be used in the similar way.

Lidocaine is another local anesthetic that may be used in the formulation. Like other amide type local anesthetic agents and unlike ester type local anesthetic agents, lidocaine has fairly good chemical stability in both low and high pH media. But its skin permeability is much better at pH about 7 than about 4. Therefore, increasing the pH of an ALA-lidocaine formulation shortly before or during application provides good chemical stability of ALA and improves the skin permeation of both ALA and lidocaine. Other amide type local anesthetic agents, such as prilocaine and bupivacaine, may be used in this design.

Therefore, another embodiment of the invention is to provide a low pH formulation comprising water, ALA and a local anesthetic agent such as tetracaine or lidocaine, and to provide a convenient method to increase the pH of the formulation prior to or during the application of the formulation on the tissues to be treated in the photodynamic therapy. One such method is to cover the formulation already applied on the tissues with a layer of material impregnated with a pH-adjusting agent(s), such as a high pH buffer. The pH of the formulation is thus rapidly increased to about 6.5 to 7 to make more tetracaine molecules unionized and more ALA molecules carrying no net charge. Unionzed tetracaine and ALA carrying no net electric charge have better skin permeability than ionized tetracaine and ALA carrying net electric charge.

Another embodiment of the invention is related to using controlled heat to improve the skin penetration of ALA, its derivatives, or other photosensitizers. The purpose of applying controlled heat is to increase penetration depth of the photosensitizer and to shorten the delivery time necessary to obtain desired penetration depth and/or concentration of the photosensitizer in the tissue. Johan Moan et al. studied the temperature dependence of ALA penetration into mouse and human skin and found that increased temperature did not cause increased penetration (3). We hypothesize that the lack of temperature dependence of the skin penetrability may have several possible causes including 1) the formulation might have a low intra-formulation ALA mobility so that the overall rate of penetration was rate-limited by the rate of release of ALA from the formulation rather than by skin permeability; and 2) the potential gain in permeability might be offset by the reduction of penetration driving force caused by increased solubility and/or increased ionization of ALA. The inventors believe that controlled heat may improve the tissue penetration of ALA if the formulation is optimized, which may mean designing the formulation such that the overall ALA skin penetration is rate-limited by the permeability of the stratum corneum, which should have significant temperature dependence. Other negative offsetting factors should be minimized or eliminated. Modifying the pH before or during the application too close to ALA's isoelectric point may offset the possible loss of penetration driving force caused by increased ionization. Heating the skin to a predetermined and relatively precise temperature range is also potentially important. As the skin is heated to a temperature much higher than a certain point (i.e. about 39 C.), the blood circulation may increase very dramatically in an attempt to bring the temperature down to normal. This dramatically increased blood circulation would carry the drug away from the skin at much faster rates. For ALA, whose targeted destinations are superficial tissues as opposed to systemic circulation, the increased elimination from the skin caused by higher than optimal heating temperatures may more than offset the gain in permeability by the same heat, resulting in a lower concentration in the target tissues. Therefore, it is important to properly design and accurately control the heating temperature range in order to gain maximum benefits.

Another embodiment of the invention relates to providing a formulation with a low pH so that ALA or its derivative is chemically stable in the formulation, and increasing the pH of the formulation via a convenient method prior to or during the application to promote the penetration of the photosensitizer into the tissues to be treated.

Yet another embodiment of the invention relates to incorporating a local anesthetic agent in the formulation containing the photosensitizer, so that the local anesthetic is delivered into the tissues along with the photosensitizer. This can eliminate or reduce the pain caused by the single oxygen or other free radicals in the photodynamic therapy.

Another embodiment of the invention relates to providing a formulation comprising ALA or its derivatives and a local anesthetic agent. The pH of the formulation is initially low so that the local anesthetic agent is chemically stable, and is increased via a convenient method prior to the application to a predetermined new pH range that promotes the penetration of the local anesthetic agent and, potentially, the photosensitizer, (depending on the type of photosensitizer) into the tissues to be treated.

An additional embodiment of the invention relates to providing a formulation comprising a photosensitizer, a conversion agent (such as a crosslinkable but substantially uncrosslinked polymer), and optionally a local anesthetic agent. The formulation is capable of being converted to a solidified sheet via a convenient method (such as via contact with a crosslinking agent) shortly prior to or during the application to facilitate the removal of the formulation from the tissues.

It is understood that the aforementioned individual embodiments (use of controlled heat, local anesthetic—photosensitizer combined formulation, pH manipulation, and the solidification of the formulation) may be combined in various ways to achieve the most desired effects and/or flexibility in the treatment.

The following are some examples which further elaborate how some of the embodiments of the invention may be utilized.

EXAMPLE 1

A commercially available aminolevulinic acid (ALA) formulation is applied to the skin cancer area of a human patient. A heating patch capable of generating controlled heat is applied over the applied ALA cream in order to heat the tissues under it to a temperature range of between 38–44 C. for 1 hour or longer. The high tissue temperature increases the depth that ALA can reach within a certain time and/or shortens the time it takes for ALA to reach therapeutic concentrations at a certain depth. After sufficient contact time, the heating patch and the ALA cream are removed and a light with proper wavelengths is irradiated onto the ALA-treated tissues to produce free oxygen for killing the cancerous cells.

The heating patch has a closed chamber defined by an air-impermeable bottom and an air-impermeable cover. The edges of the bottom and cover are joined to form a closed chamber within which a heat-generating medium resides. The cover has a predetermined number of holes with pre-determined size to allow oxygen in ambient air into the heat-generating medium at pre-determined rates. The heating patch is stored in an airtight container, such as an airtight pouch. When the heating patch is removed from the container, oxygen in ambient air flows into the heat-generating medium via the holes in the cover to start an exothermic reaction (oxidation reaction of iron powder). The number and size of the holes in the cover determine the rate at which oxygen enters the heat-generating medium, and hence regulate the heating temperature. A typical heat generating medium composition has the following weight portions:

Activated carbon: 5 portions (i.e. HDC grade Norit Americas, Inc.)
Fine iron powder: 16 portions (i.e. Grade 1430, ISP Technologies, USA)
Wood powder: 3 portions (i.e. fine wood flour, Pine, Pioneer Sawdust, US)
Sodium chloride: 2 portions
Water: 6 portions A heating patch containing 16 grams of this composition over an area of 40 cm$^2$ (with 45 0.9 mm diameter holes in the cover) is capable of heating the skin under the patch to a range of 40–43 C. for at least 4 hours. The quantity and composition of the heat-generating medium, the size of the heating patch, and the size and number of the holes in the cover can be adjusted to obtain desired heating temperature and duration.

The bottom of the heating patch may be coated with a layer of adhesive, so that the heating patch can be affixed to the skin over the ALA cream.

This method is expected to increase the penetration depth and shorten the necessary delivery time for the ALA formulation.

EXAMPLE 2

5-aminolevulinic acid hydrochloride (ALA) is mixed with a hydrogel according to a 5:95 weight ratio. The hydrogel has the composition of 5% carboxymethylcellulose (thickening agent, such as that distributed under the brand Natrasol by Aqualon, USA), 20% polyvinyl alcohol (such as polyvinyl alcohol, USP, molecular weight 31,000–50,000, distributed by Amresco), and 75% water. HCl is added into the ALA:hydrogel mixture to lower the pH to about 3. ALA in this formulation is stable because of the low pH. However, ALA would have low skin/tissue permeability if the mixture is applied unaltered onto the skin or other tissue surfaces because most of the ALA molecules carry net electric charges at this pH.

To increase the skin/tissue penetrability, the mixture is covered with a layer of fabric material impregnated with a base pH-adjusting agent after it is applied onto the skin or other tissue. The pH-adjusting agent increases the pH of the mixture to around the isoelectric point of ALA (about 6.5) to significantly reduce the number of ALA molecules that carry net electric charges, which improves the tissue penetrability. For the purpose of increasing the pH to an increased narrow range, a pH buffer system usually is better than just a base. For example, 87.7:12.3 and 68.5:31.5 (molar ratios) mixtures of monosodium phosphate and disodium phosphate (with proper buffer capacity) can buffer the pH to 6.0 and 6.5, respectively. Increasing the pH to a predetermined precise range can maximize the penetration driving force.

A number of bases may be used as the pH-adjusting agent, including but not limited to dibasic sodium phosphate ($Na_2HPO_4$), sodium hydroxide (NaOH), and tromethamine.

This method addresses the conflicting pH requirements between good chemical stability and good tissue penetrability.

EXAMPLE 3

Similar to that of Example 2, except that the low pH formulation is an oil-in-water emulsion containing 20% ALA (wt/wt) with a pH of about 3.

EXAMPLE 4

Similar to Example 2 or 3, except that a local anesthetic agent is also added to the mixture. For example, 2% tetracaine can be mixed into the mixture of Example 2. The low pH of the mixture also provides good chemical stability of tetracaine. The increased pH (in this case the pH needs to be increased to 6.5 to 7) by the pH-adjusting agent also increases skin/tissue penetrability of tetracaine, since tetracaine has much better skin permeability when the pH is above about 6.5 to 7.

The pain associated with free oxygen radicals produced by the therapy can be reduced or eliminated by using this ALA+local anesthetic formulation.

Lidocaine may also be used as the local anesthetic agent in the ALA+local anesthetic formulation. Lidocaine does not need low pH for improving chemical stability as it is quite stable even at high pH (i.e. 7). But at low pH lidocaine dissolves in aqueous formulations much better, and the complete dissolution allows lidocaine to distribute more evenly in the formulation. The concentration of lidocaine can be chosen so that lidocaine reaches or exceeds its solubility in the formulation when the pH is increased to about 6.5 to 7, which maximizes skin/tissue penetrability.

EXAMPLE 5

Similar to Example 2 or 3, except that the formulation on the skin/tissue is covered by a heating patch similar to that in Example 1, and the pH adjusting agent is coated or impregnated onto the bottom of the heating patch. In this method, the controlled heat, along with increased pH, improves the skin/tissues penetrability of ALA.

EXAMPLE 6

Similar to that of Example 4 (also include local anesthetic agent). The controlled heat improves the skin/tissue penetrability of both ALA and the local anesthetic agent.

In all of the examples above, a crosslinking agent such as sodium borate can also be incorporated into the fabric material or the bottom of the heating patch that will come in contact with the formulation that contains a crosslinkable but substantially uncrosslinked polymer (referred as conversion agent hereafter). Following the contact with the crosslinking agent, the formulation can solidify into a soft, coherent solid. This will not only make the removal of the formulation from the skin easier, but will also minimize the spreading of the formulation into areas that are not intended to be treated with the formulation. The spreading of the formulation into unintended areas may result in the delivery of the photosensitizer into the unintended areas which may cause unnecessary damages to healthy cells in the subsequent photodynamic therapy.

In this text, controlled heat means a heat that is capable of increasing the skin surface temperature to at least 35 C. but not higher than 60 C., more preferably, between 38–45 C., for an extended but predetermined period of time.

The methods and formulations in this invention can potentially improve the treatment of any diseases that can benefit from photodynamic therapy treatments, including but not limited to skin cancer, psoriasis, and acne.

What is claimed is:

1. A method for rapidly delivery of a drug to a patient comprising:
   administering dermally a photosensitizer formulation;
   applying immediately a pH modifying permeation enhancer to the photosensitizer formulation;
   applying a heating component to the skin of the user over the photosensitizer delivery site to heat underlying tissues at the site; and
   moderating a control component capable of controlling the magnitude and duration of heat generated by the heating component, to control the speed and depth of penetration of said formulation.

2. The method of claim 1, wherein a portion of the formulation is stored in skin and sub-skin tissues.

3. The method of claim 2, wherein said storage of said drug creates a depot site.

4. The method of claim 2, wherein said drug is in controlled release formulation.

5. The method of claim 2, wherein the drug is disposed in the skin tissues.

6. The method of claim 2, wherein the formulation is disposed in the sub-skin tissues.

7. The method of claim 2, wherein the formulation in the drug depot site is injected into the skin.

8. The method of claim 2, wherein the step of administering comprises implanting the formulation into the skin.

9. The method of claim 3, wherein the heating component is capable of generating heat when supplied with electric current.

10. The method of claim 9, wherein the control component receives a temperature signal from a temperature sensor proximate to the skin.

11. The method of claim 10, wherein the control component adjusts the electric current to the heating component according to the temperature sensor.

12. The method of claim 9, wherein the control component also has a mechanism to lockout a length of time in which the device generates no heating during formulation administration.

13. The method of claim 9, wherein the control component is a mechanism that allows the patient to trigger delivery of a pre-determined amount of bolus formulation from the depot site.

14. The method of claim 9, wherein the control component is pre-programmed to send an electric current with predetermined magnitude through a wire to the heating component for a pre-determined length of time.

15. The method of claim 14, wherein the magnitude and the pre-determined length of time of the current produce a temperature increase at the skin for a pre-determined length of time that releases a pre-determined amount of the formulation from the depot site.

16. The method of claim 14, wherein the magnitude of the current is designed to produce several heating temperature vs. time profiles to accommodate different needs.

17. The method of claim 1 further comprising a microprocessor in conjunction with the electric heating component.

18. The method of claim 1, wherein the heating component has a temperature sensor that measures the temperature at the drug patch and transmits the measured temperature to the control component to regulate the heating temperature.

19. The method of claim 1, wherein the heating component has a layer of thermal insulating material on the side not in contact with the skin for minimizing heat loss.

20. The method of claim 1, wherein an anesthetic is delivered concurrently with the permeation enhancer into the skin from a transdermal drug patch.

21. The method of claim 20, further comprising means for releasably affixing the heating component to the drug patch.

22. The method of claim 21, wherein the heating component and the drug patch have areas with corresponding loop and hook fasteners.

23. The method of claim 1, wherein said heating component is an exothermic oxidation heating patch.

24. The method of claim 23, wherein the heating component is a disposable heating component.

25. The method of claim 1, wherein the drug is selected from the group consisting of analgesics, anti-arthritis drugs, anti-inflammatory drugs, anti-migraine drugs, cardiovascularly active drugs, smoke cessation drugs, hormones, androgen, estrogen, non-steroidal anti-inflammatory agents, anti-hypertensive agents, analgesic agents, anti-depressants, antibiotics, anti-cancer agents, local anesthetics, antiemetics, anti-infectants, contraceptives, anti-diabetic agents, steroids, anti-allergy agents, anti-migraine agents, agents for smoking cessation, anti-obesity agents, nicotine, testosterone, estradiol nitroglycerin, clonidine, dexamethasone, wintergreen oil, tetacaine, lidocaine, fentanyl, sufentanil, alfentanil and other potent mu-receptor agonists, progesterone, insulin, vitamin A., vitamin C, vitamin E, prilocaine, bupivacine, sumatriptan, scopolamine, dihydroegotamine, and combination thereof.

* * * * *